(12) United States Patent
Karpiel et al.

(10) Patent No.: US 8,529,434 B2
(45) Date of Patent: Sep. 10, 2013

(54) ENDOSCOPIC SHEET DELIVERY

(75) Inventors: John A. Karpiel, Winston-Salem, NC (US); Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 741 days.

(21) Appl. No.: 12/605,794

(22) Filed: Oct. 26, 2009

(65) Prior Publication Data
US 2010/0106068 A1 Apr. 29, 2010

Related U.S. Application Data

(60) Provisional application No. 61/109,398, filed on Oct. 29, 2009.

(51) Int. Cl.
*A61B 1/00* (2006.01)
*A61B 18/14* (2006.01)

(52) U.S. Cl.
USPC .............................................. 600/104; 606/52

(58) Field of Classification Search
USPC ......... 606/144–215, 52; 623/23.72; 600/104
See application file for complete search history.

(56) References Cited

U.S. PATENT DOCUMENTS

| | | | |
|---|---|---|---|
| 775,985 A | 11/1904 | McKain | |
| 1,521,396 A | 12/1924 | Scott | |
| 2,609,155 A | 9/1952 | Fosnaugh | |
| 2,671,444 A | 3/1954 | Pease, Jr. | |
| 3,089,495 A | 5/1963 | Florio | |
| 3,710,400 A | 1/1973 | Sparks | |
| 4,539,716 A | 9/1985 | Bell | |
| 4,738,740 A | 4/1988 | Pinchuk | |
| 4,798,606 A | 1/1989 | Pinchuk | |
| 4,927,410 A | 5/1990 | Kovacs | |
| 5,176,642 A | 1/1993 | Clement | |
| 5,203,767 A | 4/1993 | Cloyd | |
| 5,258,000 A | 11/1993 | Gianturco | |
| 5,263,969 A | 11/1993 | Phillips | |

(Continued)

FOREIGN PATENT DOCUMENTS

| | | |
|---|---|---|
| FR | 2735015 A1 | 12/1996 |
| WO | WO 2004/012627 A1 | 2/2004 |
| WO | WO 2004/080348 A1 | 9/2004 |
| WO | WO 2007/090155 A1 | 8/2007 |

OTHER PUBLICATIONS

International Search Report/Written Opinion for PCT/US09/062066 mailed Feb 2, 2010.

(Continued)

*Primary Examiner* — Suzette J Gherbi
(74) *Attorney, Agent, or Firm* — Brinks Hofer Gilson & Lione

(57) ABSTRACT

Medical devices and related methods are provided for treating a bleeding side of an internal bodily organ that are robust and versatile for use in a variety of endoscope applications. One embodiment of a medical device includes a catheter, a sheet and elongated forceps. The catheter defines a catheter lumen and is sized to be received within the accessory channel of the endoscope. The sheet is formed of hemostatic fabric formed into a tubular configuration having opposing first and second ends. The elongated forceps have a pair of collapsible grasping jaws. The grasping jaws are collapsed around the first end of the sheet, and the grasping jaws and sheet are received within the catheter lumen.

18 Claims, 4 Drawing Sheets

(56) References Cited

U.S. PATENT DOCUMENTS

| | | | |
|---|---|---|---|
| 5,310,407 A | 5/1994 | Casale | |
| 5,316,543 A | 5/1994 | Eberbach | |
| 5,366,460 A | 11/1994 | Eberbach | |
| 5,368,602 A | 11/1994 | de la Torre | |
| 5,397,331 A | 3/1995 | Himpens et al. | |
| 5,464,403 A | 11/1995 | Kieturakis et al. | |
| 5,503,623 A | 4/1996 | Tilton, Jr. | |
| 5,643,317 A | 7/1997 | Pavcnik et al. | |
| 5,665,067 A | 9/1997 | Linder et al. | |
| 5,695,525 A | 12/1997 | Mulhauser et al. | |
| 5,788,625 A | 8/1998 | Plouhar et al. | |
| 5,873,530 A | 2/1999 | Chizinsky | |
| 5,902,228 A | 5/1999 | Schulsinger et al. | |
| 5,919,184 A | 7/1999 | Tilton, Jr. | |
| 5,947,997 A | 9/1999 | Pavcnik et al. | |
| 5,951,531 A | 9/1999 | Ferdman et al. | |
| 5,957,939 A | 9/1999 | Heaven et al. | |
| 5,972,022 A | 10/1999 | Huxel | |
| 6,007,515 A | 12/1999 | Epstein et al. | |
| 6,021,776 A | 2/2000 | Allred et al. | |
| 6,059,749 A | 5/2000 | Marx | |
| 6,077,217 A | 6/2000 | Love et al. | |
| 6,328,765 B1 * | 12/2001 | Hardwick et al. | 623/23.72 |
| 6,368,300 B1 | 4/2002 | Fallon et al. | |
| 6,425,900 B1 | 7/2002 | Knodel et al. | |
| 6,503,273 B1 * | 1/2003 | McAllister et al. | 623/1.41 |
| 6,551,333 B2 | 4/2003 | Kuhns et al. | |
| 6,610,026 B2 | 8/2003 | Cragg et al. | |
| 6,723,067 B2 | 4/2004 | Nielson | |
| 6,746,458 B1 | 6/2004 | Cloud | |
| 6,811,550 B2 | 11/2004 | Holland et al. | |
| 6,863,660 B2 | 3/2005 | Marx | |
| 7,101,862 B2 | 9/2006 | Cochrum et al. | |
| 7,156,880 B2 | 1/2007 | Evans et al. | |
| 7,485,124 B2 | 2/2009 | Kuhns et al. | |
| 7,641,836 B2 | 1/2010 | Li et al. | |
| 7,670,362 B2 | 3/2010 | Zergiebel | |
| 7,673,783 B2 | 3/2010 | Morgan et al. | |
| 7,753,934 B2 | 7/2010 | Wilk | |
| 7,780,973 B2 | 8/2010 | Freeman et al. | |
| 7,846,199 B2 * | 12/2010 | Paul et al. | 623/1.24 |
| 7,871,434 B2 * | 1/2011 | Case et al. | 623/2.12 |
| 7,919,112 B2 * | 4/2011 | Pathak et al. | 424/426 |
| 8,109,995 B2 * | 2/2012 | Paniagua et al. | 623/2.14 |
| 8,203,029 B2 * | 6/2012 | Gibbins et al. | 602/48 |
| 2001/0034509 A1 | 10/2001 | Cragg et al. | |
| 2003/0181917 A1 | 9/2003 | Gertner | |
| 2003/0216695 A1 | 11/2003 | Yang | |
| 2003/0236573 A1 | 12/2003 | Evans et al. | |
| 2005/0070848 A1 | 3/2005 | Kim et al. | |
| 2005/0137577 A1 * | 6/2005 | Heruth et al. | 604/536 |
| 2005/0171562 A1 | 8/2005 | Criscuolo et al. | |
| 2005/0182445 A1 | 8/2005 | Zamierowski | |
| 2005/0277981 A1 | 12/2005 | Maahs et al. | |
| 2006/0004248 A1 | 1/2006 | Kute et al. | |
| 2006/0190016 A1 * | 8/2006 | Onuki et al. | 606/144 |
| 2008/0004657 A1 * | 1/2008 | Obermiller et al. | 606/213 |
| 2008/0048002 A1 | 2/2008 | Smith et al. | |
| 2008/0058710 A1 | 3/2008 | Wilk | |
| 2008/0114451 A1 * | 5/2008 | Stucke et al. | 623/1.46 |
| 2008/0195121 A1 | 8/2008 | Eldar et al. | |
| 2008/0208219 A1 | 8/2008 | Suzuki | |
| 2009/0062907 A1 * | 3/2009 | Quijano et al. | 623/1.24 |
| 2009/0182192 A1 * | 7/2009 | Shiono et al. | 600/103 |
| 2009/0234374 A1 | 9/2009 | Gabel et al. | |
| 2009/0234380 A1 | 9/2009 | Gabel et al. | |
| 2009/0248056 A1 | 10/2009 | Gabel et al. | |
| 2009/0270789 A1 * | 10/2009 | Maxymiv et al. | 604/22 |
| 2009/0326577 A1 * | 12/2009 | Johnson et al. | 606/213 |
| 2010/0030246 A1 * | 2/2010 | Pavcnik et al. | 606/157 |
| 2010/0030259 A1 * | 2/2010 | Pavcnik et al. | 606/215 |
| 2010/0042045 A1 | 2/2010 | Splvey | |
| 2010/0049219 A1 | 2/2010 | Cronin et al. | |
| 2010/0087854 A1 | 4/2010 | Stopek et al. | |
| 2010/0137796 A1 | 6/2010 | Perry et al. | |
| 2010/0147990 A1 | 6/2010 | McLawhorn | |
| 2010/0249895 A1 * | 9/2010 | Ramos Clamote et al. | 623/1.11 |
| 2011/0106240 A1 * | 5/2011 | Chuter | 623/1.22 |

OTHER PUBLICATIONS

International Search Report/Written Opinion for PCT/US09/067511 mailed Aug 3, 2010.
Article 34 Amendment for PCT/US09/062066.
International Preliminary Report on Patentability for PCT/US2009/062066.

* cited by examiner

ENDOSCOPIC SHEET DELIVERY

CROSS-REFERENCE TO RELATED APPLICATIONS

This application claims the benefit of U.S. Provisional Application Ser. No. 61/109,398 filed on Oct. 29, 2008, entitled "ENDOSCOPIC SHEET DELIVERY" the entire contents of which are incorporated herein by reference.

FIELD OF THE INVENTION

The present invention relates generally to endoscopic procedures, and more particularly relates to controlling bleeding of internal bodily structures.

BACKGROUND

Openings or perforations in the walls of internal organs and vessels may be naturally occurring, or formed intentionally or unintentionally. These openings may be used to gain access to adjacent structures of the body, such techniques being commonly referred to as translumenal procedures. For example, culdoscopy was developed over 70 years ago, and involves transvaginally accessing the peritoneal cavity by forming an opening in the cul de sac. This access to the peritoneal cavity allows medical professionals to visually inspect numerous anatomical structures, as well as perform various procedures such as biopsies or other operations, such as tubal ligation. Many translumenal procedures for gaining access to various body cavities using other bodily lumens have also been developed. Natural orifices such as the mouth, nose, ear, anus or vagina may provide access to such bodily lumens and cavities. The bodily lumen(s) of the gastrointestinal tract are often endoscopically explored and can be utilized to provide access to the peritoneal cavity and other body cavities, all in a minimally invasive manner.

Compared to traditional open surgery or laparoscopic surgery, translumenal procedures are less invasive by eliminating abdominal incisions (or other exterior incisions) and incision related complications, while also reducing postoperative recovery time, reducing pain, and improving cosmetic appearance. At the same time, there remain challenges to translumenal procedures, including providing a suitable conduit to the openings and body cavities, robust medical devices that are maneuverable via the conduit and operable within the body cavity, sterility of the conduit, maintaining insufflation of the body cavity, proper closure of the opening and prevention of infection. These procedures carry the risk of perforating structures that lie just beyond the bodily wall being cut or within the cavity being explored or worked within. For example, when incising the gastric wall, the potential of hitting blood vessels without knowing could lead to bleeding complications. Accidentally puncturing the small intestines could lead to the spillage of bacteria into the peritoneal cavity.

BRIEF SUMMARY

The present invention provides medical devices and methods for treating a defect of an internal bodily organ that are robust and versatile for use in a variety of endoscope applications. One embodiment of a medical device, constructed in accordance with the teachings of the present invention, includes a catheter, a sheet and elongated forceps. The catheter defines a catheter lumen and is sized to be received within the accessory channel of the endoscope. The sheet is formed of hemostatic fabric formed into a tubular configuration having opposing first and second ends. The elongated forceps have a pair of collapsible grasping jaws. The grasping jaws are collapsed around the first end of the sheet, and the grasping jaws and sheet are received within the catheter lumen.

According to more details aspects, the sheet may be rolled, folded or twisted in the tubular configuration. As one example, the corners of the sheet may be drawn together to form the first end of the tubular configuration and grasped by the grasping jaws. Similarly, the central portion of the sheet is preferably located at the second end of the tubular configuration. The sheet may be initially hydrated with an evaporative fluid, such as isopropyl alcohol, to facilitate loading the sheet into the catheter. The sheet may also be formed of a resorbable material, and more preferably is formed of an extra cellular matrix (ECM) material (e.g. subintestinal submucosa (SIS)), and most preferably is formed of an expanded ECM material (e.g. sodium hydroxide treated small intestinal submucosa (SHISH)). The sheet may be compressed within the catheter lumen and expands when outside the catheter lumen.

Another embodiment, constructed in accordance with the teachings of the present invention, provides a method for treating a defect side of an internal bodily organ via the accessory channel of an endoscope. A medical device is provided having a catheter, a sheet of hemostatic fabric and elongated forceps, such as the device described above. The sheet is formed into a tubular configuration having opposing first and second ends. The first end of the sheet is grasped within the grasping jaws of the forceps. The forceps are translated relative to the catheter to draw the sheet within the catheter lumen. The medical device is delivered to the bleeding site via the accessory channel of the endoscope. The forceps are translated relative to the catheter to place the sheet outside of the catheter lumen at a location proximate the defect site.

According to more detailed aspects, the method may further comprise the method of hydrating the sheet with an evaporative fluid prior to the step of translating the forceps relative to the catheter to draw the sheet within the catheter lumen. For example, soaking the sheet with isopropyl alcohol or other evaporative fluid facilitates loading the sheet within the catheter. As the evaporative fluid readily evaporates, the method may further comprise the step of dehydrating the sheet prior to the step of translating the forceps relative to the catheter to place the sheet outside of the catheter lumen proximate the bleeding site. The sheet may also be twisted during the step of loading the sheet within the catheter during the step of translating the forceps relative to the catheter to facilitate drawing the sheet into the catheter lumen. The method may also include manipulating the sheet with the forceps to spread out the sheet and cover the bleeding site. The forceps may be hot forceps connected to a source of electricity, and the method may further comprise the step of cauterizing the bleeding site with the hot forceps.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION

In the present application, the term "proximal" refers to a direction that is generally towards a physician during a medical procedure, while the term "distal" refers to a direction that is generally towards a target site within a patient's anatomy during a medical procedure.

Figure 1:
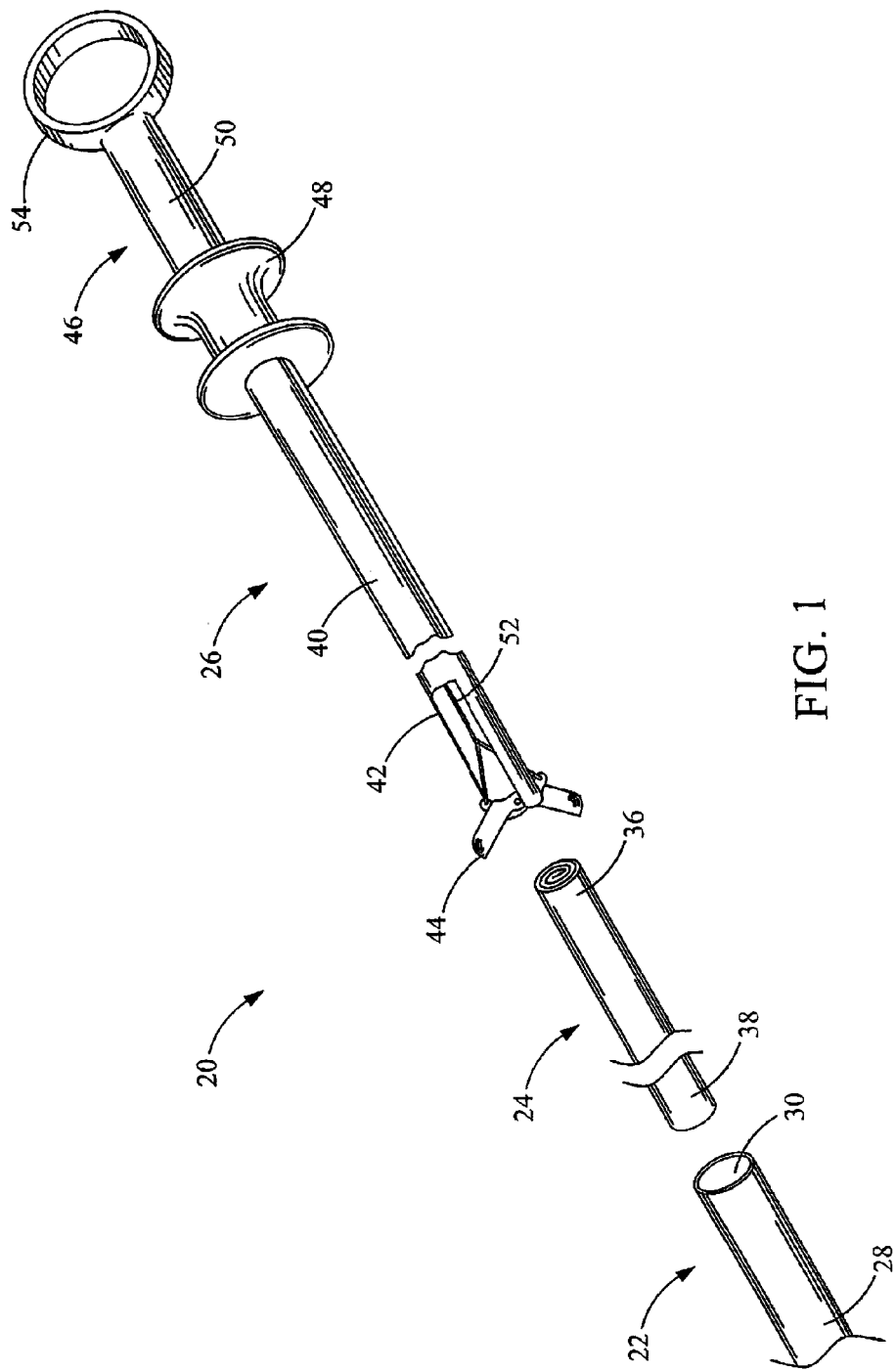
FIG. 1 is an exploded view of an embodiment of the medical device constructed in accordance with the teachings of the present invention.

Turning now to the figures, FIG. 1 depicts a medical device 20 constructed in accordance with the teachings of the present invention. The medical device generally comprises a catheter 22, a sheet of material 24 and elongated forceps 26. The catheter 22 generally includes an elongated tubular body 28 defining a catheter lumen 30. The catheter is preferably sized to be received within the working channel of an endoscope (not shown) and preferably has a size in the range of about 6 French to about 20 French, and most preferably about 10 French. The catheter 22 is used to deliver the sheet material 24 to a defect of an internal bodily organ such as a bleeding site to provide hemostasis, reinforcement and sealing at the site. As will be described further below, the forceps 26 are used to both load the sheet 24 as well as deliver the sheet 24 to the bleeding site.

Figure 2:
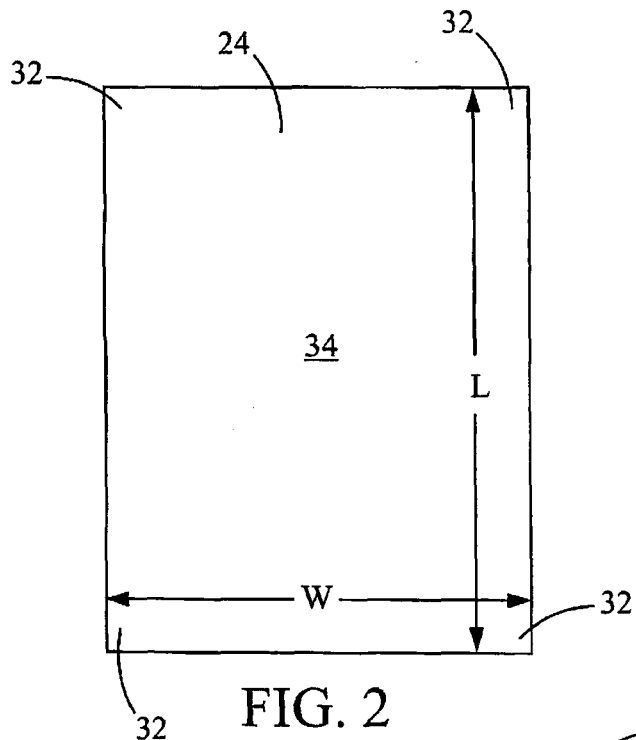
FIG. 2 is a plan view of a sheet of hemostatic fabric forming a portion of the medical device depicted in FIG. 1.

The sheet 24 is preferably formed of a hemostatic material, which as used herein includes sheets of material that promote hemostasis, including knitted, woven or non-woven fabrics, gauze, meshes, sponge sheets, foam sheets, plastic sheets, tissue layers and ECM materials. Synthetic materials may also be used, e.g. PIFE, polypropylene, and polyester fabrics or meshes and the like. The sheet 24 may have many different forms and shapes such a round, square, rectangular, triangular, etc. A rectangular sheet 24 is shown laid out in FIG. 2, and preferably has a width W between about 1 cm to about 5 cm, and a length of about 2 cm to about 15 cm. Most preferably the sheet 24 is about 2 cm by wide by about 8 cm long.

One preferred class of hemostatic materials formed as sheets include extracellular matrix (ECM) materials. For example, the sheet 24 may comprise small intestinal submucosa (SIS), such those sold under the trademarks BIODESIGN™ SURGISIS® Hernia Repair Graft, available from Cook Medical Inc., of Bloomington, Ind., which provides smart tissue remodeling through its three-dimensional extracellular matrix (ECM) that is colonized by host tissue cells and blood vessels, and provides a scaffold for connective and epithelial tissue growth and differentiation along with the ECM components. Preferably, the sheet 24 would be a one to four layer soft tissue graft made from any number of tissue engineered products, and can be lyophilized or non-lyophilized. Reconstituted or naturally-derived collagenous materials can be used, and such materials that are at least bioresorbable will provide an advantage, with materials that are bioremodelable and promote cellular invasion and ingrowth providing particular advantage. Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The sheet 24 may also comprise a composite of a biomaterial and a biodegradeable polymer. Additional details may be found in U.S. Pat. No. 6,206,931 to Cook et al., the disclosure of which is incorporated herein by reference in its entirety.

Additionally, the ECM material of the invention can be subjected to processes that expand the material. In certain forms, such expanded material can be formed by the contacting the ECM material with one or more alkaline substances until the material expands. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner. Illustratively, the expanded material can be enriched with bioactive components, dried, and/or molded, etc., in the formation of a sheet of a desired shape or configuration. In certain embodiments, an expanded ECM material construct an be highly compressible and expandable such that the material can be compressed for delivery, such as from within the lumen of a cannulated delivery device, and thereafter expand upon deployment from the device so as to become anchored within a patient, cause closure of a tract within the patient, and/or cause hemostasis.

Expanded ECM materials can be formed by the controlled contact of the inventive ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded. The ECM material will typically include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness. An expanded ECM material typically appears more porous than a corresponding non-expanded ECM material. Moreover, in many instances, the expanded ECM material can be demonstrated as having increased porosity, e.g., by measuring for an increased permeability to water or other fluid passage as compared to the non-treated starting material. The more foamy and porous structure of an expanded ECM material can allow the material to be cast or otherwise prepared into a variety of shapes (including a tubular configuration) for use in the preparation of medical materials and devices. Further details may be found in U.S. patent application Ser. Nos. 12/488,974 and 12/488,996 filed Jun. 22, 2009 and PCT/US09/49079 filed Jun. 29, 2009, the disclosures of which are hereby incorporated by reference in their entirety.

Figure 3:
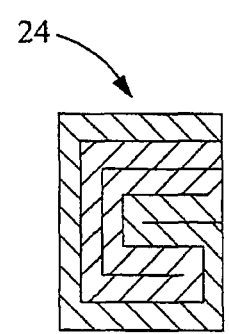
FIG. 3 is a cross-sectional view of an alternate embodiment of a sheet of hemostatic fabric forming a portion of the medical device depicted in FIG. 1.
Figure 4:
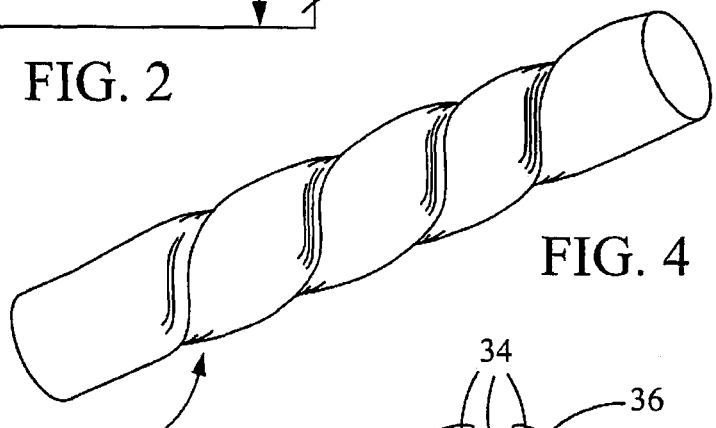
FIG. 4 is perspective view of another alternate embodiment of a sheet of hemostatic fabric forming a portion of the medical device depicted in FIG. 1.
Figure 5:
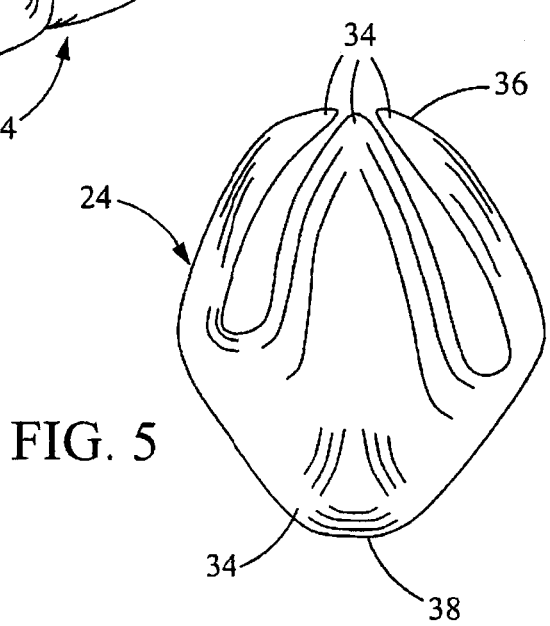
FIG. 5 is a front view of yet another alternate embodiment of a sheet of hemostatic fabric forming a portion of the medical device depicted in FIG. 1.

The sheet 24 generally has corners 32 surrounding a central portion 34 of the sheet. The sheet 24 of hemostatic fabric is formed into a tubular configuration for being grasped by the forceps 26 and loaded within the lumen 30 of the catheter 22. By way of example, FIG. 1 shows the sheet 24 being rolled into a cylindrical shape. FIG. 3 shows a cross-sectional view of the sheet 24 being folded over onto itself into a tubular shape having a generally square cross-section. In FIG. 3, the sheet 24 has been folded along its length, and folded in half, and again in half, and again in half. FIG. 4 shows the sheet being twisted into a spiral configuration. It will be recognized by those skilled in the art that both the rolled and folded sheets disclosed in FIGS. 1 and 3 may be subsequently twisted as shown in FIG. 4. In the embodiment of FIG. 5, the sheet 24 has been folded by drawing the corners 32 of the sheet 24 together at the first end 36, while the central portion 34 remains at the second end 38 of the sheet 24. The fabric disposed between the ends 36, 38 of the sheet 24 in the embodiment of FIG. 5, may be further folded, rolled or twisted to form the tubular configuration of the sheet 24.

Figure 6:
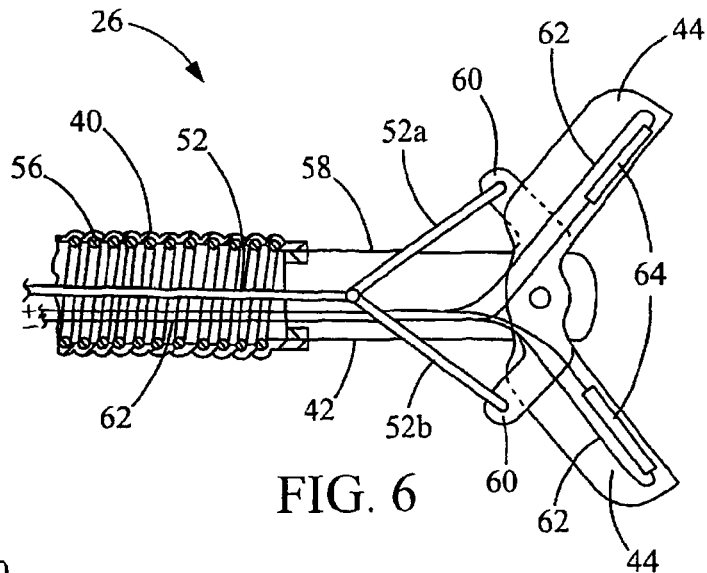
FIG. 6 is a side view, partially in cross-section and partially schematic, of forceps forming a portion of the medical device depicted in FIG. 1.

The forceps 26 are generally designed to grasp the first end 36 of the sheet 24 in its tubular configuration, and both load the sheet 24 into the catheter 28 as well as deliver the sheet 24 through the catheter 22. As used herein, "forceps" includes any elongated surgical instrument for grasping and holding objects, including pinchers, tongs, clamps and the like. Generally, the elongated forceps 26 include an elongated main body 40 having a distal end 42 that supports a pair of collapsible jaws 44. As shown in FIG. 1, a proximal end of the elongated forceps 26 defines a handle assembly 46 which includes a spool 48 connected to the main body 40 and a control rod 50 connected to a control wire 52 for operating the jaws 44. A thumb ring 54 is connected to the control rod 50 to facilitate manipulation thereof. As best seen in FIG. 6, the main body 40 preferably comprises a helically wound coil 56 having a protective coating disposed thereon. The control wire 52 bifurcates into wires 52a and 52b for connection to the jaws 44. A support body 58 is connected to the main body 40 and is pivotally connected to the jaws 44, which in turn include linkages 60 attached to the control wire 52, 52a, 52b. The forceps 26 are preferably hot forceps, and thus include wires 62 linked to resistance heating elements 64 attached to each jaw 44. The heating elements have much lower electrical resistance than the steel typically used for forcep jaws. Various types of forceps may be used in the medical device 20 as will be recognized by those skilled in the art, including other "hot" forceps, such as monopolar and bipolar electrosurgical forceps, in which the tissue is the resistive element in the circuit, as is known in the art.

Figure 7:
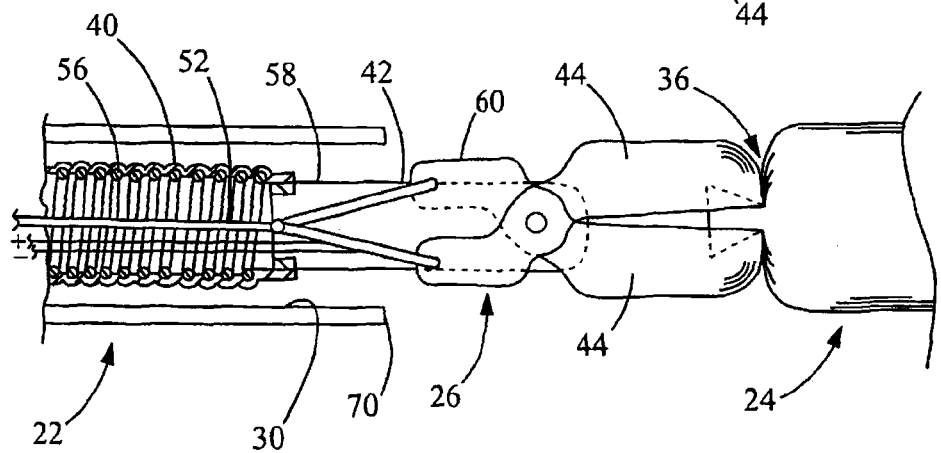
FIG. 7 is a side view of the medical device depicted in FIG. 1 showing operation of the device.
Figure 8:
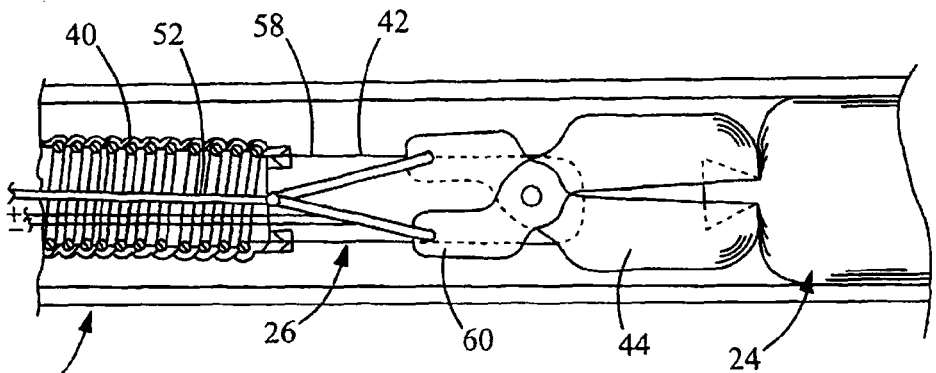
FIG. 8 is a side view of the medical device depicted in FIG. 1, showing operation of the device.

A method of employing the medical device 20 will now be described with reference to FIGS. 1 and 7 through 9. As shown in FIG. 7, the elongated forceps 26 are placed through the lumen 30 of the catheter 22 such they extend beyond the distal end 70 of the catheter 22. The jaws 44 of the forceps 26 are collapsed around the first end 36 of the tubular configuration of the sheet 24 by manipulating the handle assembly 46. The tubular configuration of the sheet 24 is preferably formed to have a larger outer diameter than the inner diameter of the catheter lumen 30. While grasping the sheet 24, the forceps 26 are translated relative to the catheter 22 to draw the sheet 24 within the catheter lumen 30, as shown in FIG. 8. Preferably, the tubular configuration of the sheet 24 is somewhat compressed during this process. To aid in fitting the sheet 24 into the catheter 22, the sheet 24 is preferably soaked in an evaporative fluid such as isopropyl alcohol (IPA). As used herein, an evaporative fluid is a fluid that substantially evaporates at room temperature and atmospheric pressure within a few hours (e.g. 3-4 hours) and preferably within a few minutes. This makes the sheet 24 much easier to work with, reduces friction while loading it in the catheter 22, and makes the material easier to compress. With the combination of the sheet 24 being pulled by the forceps 26, and the catheter 22 being pulled over the sheet 24, the tubular configuration of the sheet 24 can be loaded into distal end 70 of the catheter 22 in a compressed state. Twisting and folding of the sheet 24, not only prior to, but also during this loading process aides in loading the sheet 24 into the catheter 22.

To deploy the sheet 24, the catheter 22 may be passed through the accessory channel of an endoscope (not shown). This is a significant advantage in that other devices typically require the use of exterior channels of a scope, and these exterior channels make retro-flexion of the endoscope more difficult. As will be appreciated by those skilled in the art, the catheter 22 can then be navigated to the bleeding site, and preferably is placed in close proximity thereto. Once in place, the forceps 26 are advanced distally to push the sheet 24 out of the catheter 22 at the desire location. The catheter 22 may also be translated proximally to assist in deploying the sheet 24. During this step, pressure on the control rod 50 of the handle assembly 46 should be maintained to keep the forcep jaws 44 closed to reduce the friction encountered with the catheter 22, as the jaws 44 tend to open as they are pushed forward. The handle 46 is manipulated to open the jaws 44 and release the sheet 24.

Figure 9:
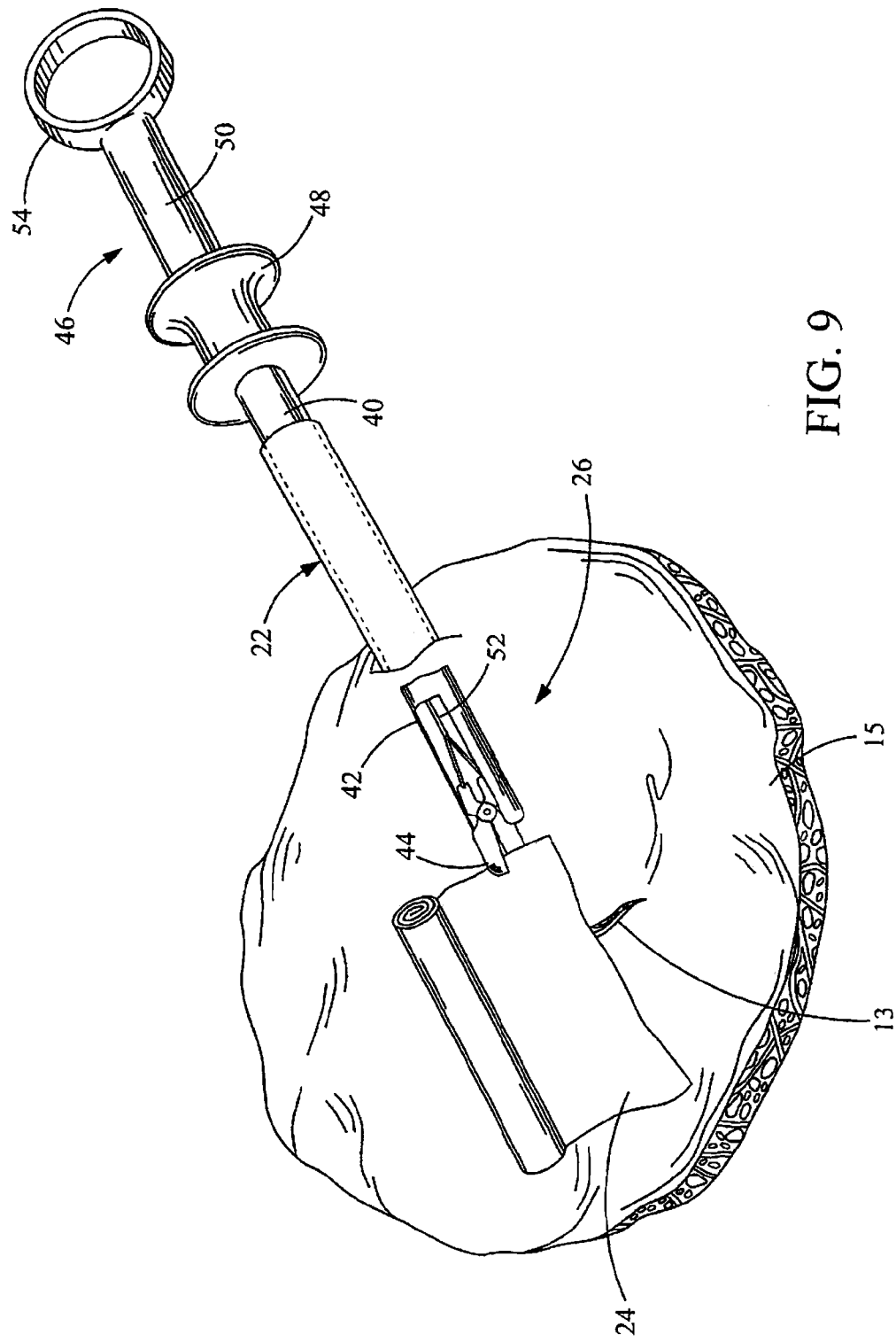
FIG. 9 is a perspective view showing operation of the medical device depicted in FIG. 1.

As also shown in FIG. 9, the forceps 26 may be used to manipulate the sheet 24, and in particular lay the sheet out by unrolling, unfolding or otherwise manipulating the tubular configuration of sheet 24. The forceps 26 may also be used to grasp the sheet 24 and properly place the sheet over the bleeding site 13 in the tissue 15. Similarly, because the forceps 26 are preferably hot forceps, they be energized to heat the jaws 44 and used to cauterize the tissue 15 at the bleeding site 13. The forceps 26 may also be used to apply pressure to the sheet against the tissue 15. The sheet 24 will naturally absorb fluid at the bleeding site 13 and adhere thereto. Additional fastening elements may also be employed as is known in the art. See, e.g. U.S. patent application Ser. No. 12/428, 226 filed Apr. 22, 2009, Ser. No. 12/557,232, filed Sep. 10, 2009, and Ser. No. 12/557,204, filed Sep. 10, 2009, the disclosures of which are incorporated by reference herein. To finish the procedure, the forceps 26 may be drawn within the catheter 22 and together moved proximally through the accessory channel of the endoscope.

Accordingly, it will be recognized by those skilled in the art that the medical devices and methods of the present invention allow the hemostatic fabric to be delivered through the accessory channel of an endoscope, thereby overcoming the drawbacks of many other systems which require the device to be back-loaded into the endoscope. Likewise, the endoscope may still be retroflexed and otherwise manipulated to perform complex procedures within the patient. The medical device is robust and through the use of forceps is quite versatile in allowing manipulation of the hemostatic fabric as well as cauterizing of the bleeding site.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for treating a defect of an internal bodily organ via the accessory channel of an endoscope, the medical device comprising:
    a catheter defining a catheter lumen;
    a sheet of material formed into a tubular configuration having opposing first and second ends, the sheet initially hydrated with an evaporative fluid comprising alcohol;
    an elongated forceps having a pair of collapsible grasping jaws;
    the grasping jaws collapsed around the first end of the sheet;
    wherein the grasping jaws and sheet are in a loaded configuration within the catheter lumen with the sheet in a hydrated condition being hydrated by the evaporative fluid.

2. The medical device of claim 1, wherein the sheet is rolled into a cylindrical shape defining the tubular configuration.

3. The medical device of claim 1, wherein the sheet is folded over onto itself in the tubular configuration.

4. The medical device of claim 1, wherein the sheet is twisted into a cylindrical shape defining the tubular configuration.

5. The medical device of claim 1, wherein the corners of the sheet are drawn together to form the first end of the sheet grasped by the grasping jaws.

6. The medical device of claim 1, wherein a central portion of the sheet is located at the second end of the tubular configuration.

7. The medical device of claim 1, wherein the evaporative fluid is isopropyl alcohol.

8. The medical device of claim 1, wherein the sheet is formed of a hemostatic material.

9. The medical device of claim 1, wherein the sheet is formed of a resorbable material, and wherein the resorbable material is an expanded ECM material that is compressible.

10. The medical device of claim 1, wherein the sheet is compressed within the catheter lumen and naturally expands when outside the catheter lumen.

11. The medical device of claim 1, wherein the sheet, in a planar configuration, has a length between about 2 cm to 15 cm, and has a width between about 1 cm to 5 cm, and wherein the catheter is about 8 French to 20 French.

12. A method for treating a defect of an internal bodily organ via the accessory channel of an endoscope, the method comprising the steps of:
    providing a medical device having a catheter defining a catheter lumen, a sheet of material, and an elongated forceps having a pair of collapsible grasping jaws;
    forming the sheet into a tubular configuration having opposing first and second ends;
    hydrating the sheet with an evaporative fluid;
    grasping the first end of the sheet with the grasping jaws of the forceps;
    translating the forceps relative to the catheter to draw the hydrated sheet within the catheter lumen to define a loaded configuration of the medical device where the sheet is in a hydrated condition within the lumen;
    delivering the medical device to the defect; and
    translating the forceps relative to the catheter to place the sheet outside of the catheter lumen at a location proximate the defect.

13. The method of claim 12, wherein the sheet includes at least three corners, and wherein the forming step includes collecting the corners of the sheet at the first end of the tubular configuration of the sheet.

14. A method for treating a defect of an internal bodily organ via the accessory channel of an endoscope, the method comprising the steps of:
    providing a medical device having a catheter defining a catheter lumen, a sheet of material, and an elongated forceps having a pair of collapsible grasping jaws;
    forming the sheet into a tubular configuration having opposing first and second ends;
    hydrating the sheet with an evaporative fluid;
    grasping the first end of the sheet with the grasping jaws of the forceps;
    translating the forceps relative to the catheter to draw the hydrated sheet within the catheter lumen;
    delivering the medical device to the defect;
    translating the forceps relative to the catheter to place the sheet outside of the catheter lumen at a location proximate the defect; and
    dehydrating the sheet prior to the step of translating the forceps relative to the catheter to place the sheet outside of the catheter lumen at a location proximate the bleeding site.

15. The method of claim 12, further comprising the step of twisting the sheet during the step of translating the forceps relative to the catheter to assist with drawing the sheet into the catheter lumen.

16. The method of claim 12, further comprising the step of manipulating the sheet with the forceps to spread out the sheet and cover the bleeding site.

17. The method of claim 12, wherein the forceps are hot forceps connected to a source electricity, and further comprising the step of cauterizing the bleeding site with the hot forceps.

18. The method of claim 12, wherein the forming step includes at least one of rolling and folding the sheet, and wherein the forming step further includes twisting the rolled or folded sheet.

* * * * *

UNITED STATES PATENT AND TRADEMARK OFFICE
CERTIFICATE OF CORRECTION

PATENT NO. : 8,529,434 B2  
APPLICATION NO. : 12/605794  
DATED : September 10, 2013  
INVENTOR(S) : Karpiel et al.

Page 1 of 1

It is certified that error appears in the above-identified patent and that said Letters Patent is hereby corrected as shown below:

<u>On the Title Page</u>

(60) Please delete "Oct. 29, 2009" and insert --Oct. 29, 2008--.

Signed and Sealed this  
Twenty-ninth Day of October, 2013

Teresa Stanek Rea  
*Deputy Director of the United States Patent and Trademark Office*